US012656524B2

(12) United States Patent
Tao et al.

(10) Patent No.: US 12,656,524 B2
(45) Date of Patent: Jun. 16, 2026

(54) METHOD FOR DELINEATING EXPLORATION RESERVED AREAS OF DEEP-SEA POLYMETALLIC SULFIDE RESOURCES

(71) Applicant: SECOND INSTITUTE OF OCEANOGRAPHY, MINISTRY OF NATURAL RESOURCES, Hangzhou (CN)

(72) Inventors: Chunhui Tao, Hangzhou (CN); Shili Liao, Hangzhou (CN); Guoyin Zhang, Hangzhou (CN); Xianming Deng, Hangzhou (CN); Yuan Wang, Hangzhou (CN); Jin Liang, Hangzhou (CN); Jianping Zhou, Hangzhou (CN)

(73) Assignee: SECOND INSTITUTE OF OCEANOGRAPHY, MINISTRY OF NATURAL RESOURCES, Hangzhou (CN)

( * ) Notice: Subject to any disclaimer, the term of this patent is extended or adjusted under 35 U.S.C. 154(b) by 458 days.

(21) Appl. No.: 18/302,774

(22) Filed: Apr. 18, 2023

(65) Prior Publication Data

US 2023/0258841 A1 Aug. 17, 2023

Related U.S. Application Data

(63) Continuation of application No. PCT/CN2021/115525, filed on Aug. 31, 2021.

(30) Foreign Application Priority Data

Oct. 29, 2020 (CN) .......................... 202011187687.6

(51) Int. Cl.
*G01V 9/00* (2006.01)
*G01N 33/20* (2019.01)

(52) U.S. Cl.
CPC ............... *G01V 9/00* (2013.01); *G01N 33/20* (2013.01)

(58) Field of Classification Search
CPC ................................. G01V 9/00; G01N 33/20
See application file for complete search history.

(56) References Cited

U.S. PATENT DOCUMENTS 10,077,656 B1 9/2018 Sun et al.

FOREIGN PATENT DOCUMENTS

CN 103605168 A 2/2014
CN 103886383 A 6/2014
(Continued)

OTHER PUBLICATIONS

English translation of Tao Chunhui, Deng Xianming et al, CN103605168A (Year: 2014).*
(Continued)

*Primary Examiner* — Andrew Schechter
*Assistant Examiner* — Ethan Wesley Edwards
(74) *Attorney, Agent, or Firm* — Wiersch Law Group

(57) ABSTRACT

The present application discloses a method for delineating exploration reserved areas of deep-sea polymetallic sulfide resources, which is suitable for delineating the exploration reserved area for further exploration by delineation and evaluation of the prospect area after prospecting and investigation of seabed sulfide. The method comprises the following: a stage of extracting prospecting indicators; a stage of evaluating metallogenic prospect areas; and, a stage of delineation of the exploration reserved areas. The present application can be applied to the evaluation and prediction of deep-sea polymetallic sulfide resources, in particular to the delineation of exploration reserved areas for deep-sea polymetallic sulfide resources.

5 Claims, 2 Drawing Sheets

(56)                    References Cited

FOREIGN PATENT DOCUMENTS

| | | | |
|---|---|---|---|
| CN | 107608006 A | 1/2018 |
| CN | 108287373 A | 7/2018 |
| CN | 108535791 A | 9/2018 |
| CN | 108614087 A | 10/2018 |
| CN | 109188556 A | 1/2019 |
| CN | 112379461 A | 2/2021 |
| JP | 2018059888 A | 4/2018 |
| KR | 20110012501 A | 2/2011 |
| RU | 2215309 C1 | 10/2003 |
| WO | 2018212680 A1 | 11/2018 |

OTHER PUBLICATIONS

English translation of Tao Chunhui, Pan Donglei et al, CN109188556A (Year: 2019).*
International Search Report (PCT/CN2021/115525); Date of Mailing: Nov. 22, 2021.
First Office Action(CN202011187687.6); Date of Mailing: Oct. 24, 2022.
The-Distribution-Characteristics-of-Hydrothermal-Plume-in-Mid-Ocean-Ridge-and-Its-Indicative-Role-in-Polymetallic-Sulfide-Prospecting.
Notice of Allowance(CN202011187687.6); Date of Mailing: May 30, 2023.
Prediction-of Seafloors-Polymetallic-Sulphides-Resources-in-the-North-Atlantic-Ridge-Area.
Study-on-quantitative-prediction-methods-for-polymetallic-sulfide-deposits-on-the-seabed-Take the South Atlantic (Mechanical translation).
Mining-mineral-resources-from-the-seabed: Opportunities-and-challenges.

* cited by examiner 1.1 Extracting six kinds of prospecting indicators: (1) plume information, (2) geophysical information, (3) geochemical information, (4) biological information, (5) wall rock alteration information and (6) mineralized outcrop information

↓

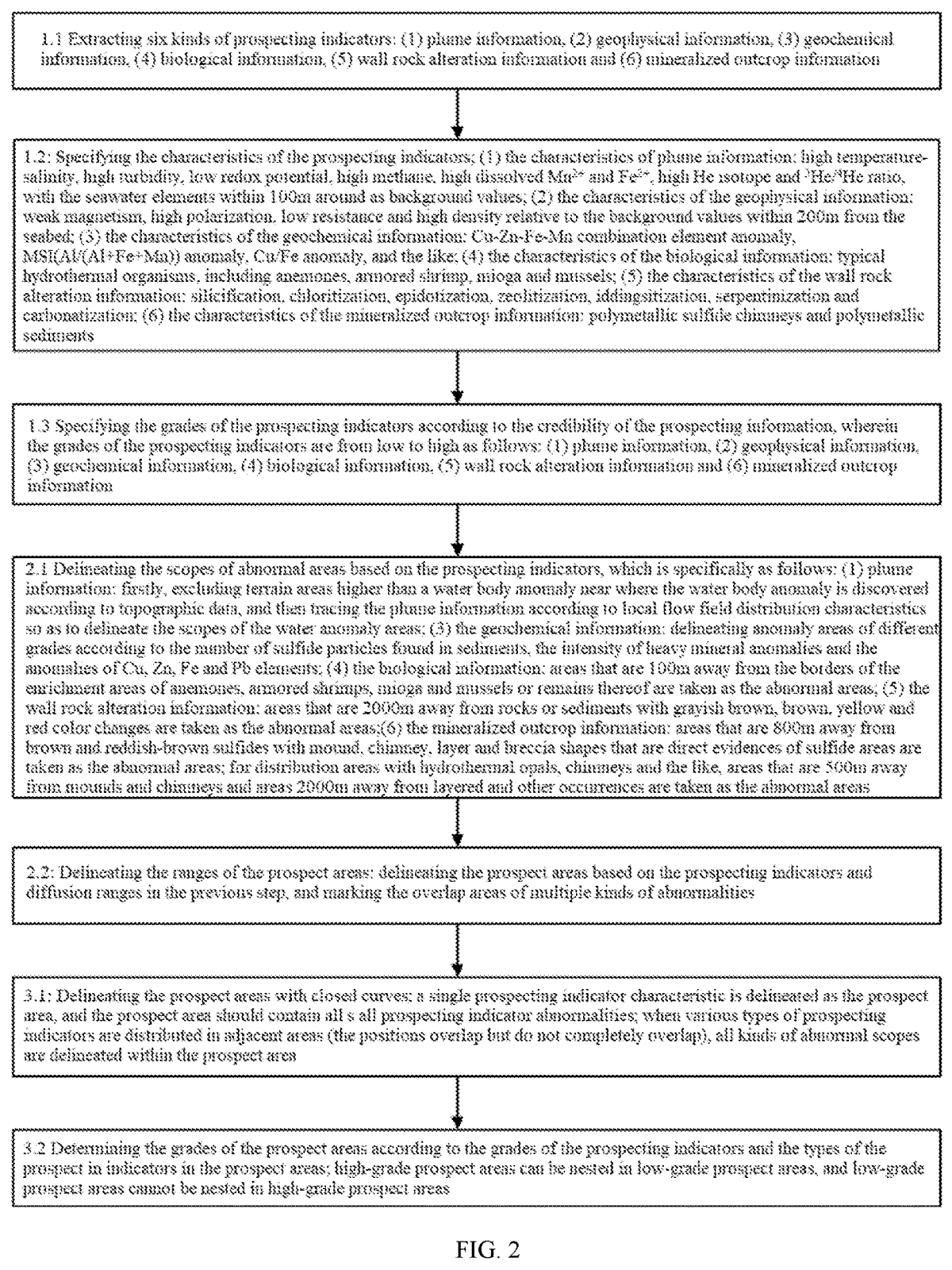

1.2: Specifying the characteristics of the prospecting indicators: (1) the characteristics of plume information: high temperature-salinity, high turbidity, low redox potential, high methane, high dissolved $Mn^{2+}$ and $Fe^{2+}$, high He isotope and $^3He/^4He$ ratio, with the seawater elements within 100m around as background values; (2) the characteristics of the geophysical information: weak magnetism, high polarization, low resistance and high density relative to the background values within 200m from the seabed; (3) the characteristics of the geochemical information: Cu-Zn-Fe-Mn combination element anomaly, MSI(Al/(Al+Fe+Mn)) anomaly, Cu/Fe anomaly, and the like; (4) the characteristics of the biological information: typical hydrothermal organisms, including anemones, armored shrimp, mioga and mussels; (5) the characteristics of the wall rock alteration information: silicification, chloritization, epidotization, zeolitization, iddingsitization, serpentinization and carbonatization; (6) the characteristics of the mineralized outcrop information: polymetallic sulfide chimneys and polymetallic sediments

↓

1.3 Specifying the grades of the prospecting indicators according to the credibility of the prospecting information, wherein the grades of the prospecting indicators are from low to high as follows: (1) plume information, (2) geophysical information, (3) geochemical information, (4) biological information, (5) wall rock alteration information and (6) mineralized outcrop information

↓

2.1 Delineating the scopes of abnormal areas based on the prospecting indicators, which is specifically as follows: (1) plume information: firstly, excluding terrain areas higher than a water body anomaly near where the water body anomaly is discovered according to topographic data, and then tracing the plume information according to local flow field distribution characteristics so as to delineate the scopes of the water anomaly areas; (3) the geochemical information: delineating anomaly areas of different grades according to the number of sulfide particles found in sediments, the intensity of heavy mineral anomalies and the anomalies of Cu, Zn, Fe and Pb elements; (4) the biological information: areas that are 100m away from the borders of the enrichment areas of anemones, armored shrimps, mioga and mussels or remains thereof are taken as the abnormal areas; (5) the wall rock alteration information: areas that are 2000m away from rocks or sediments with grayish brown, brown, yellow and red color changes are taken as the abnormal areas;(6) the mineralized outcrop information: areas that are 800m away from brown and reddish-brown sulfides with mound, chimney, layer and breccia shapes that are direct evidences of sulfide areas are taken as the abnormal areas; for distribution areas with hydrothermal opals, chimneys and the like, areas that are 500m away from mounds and chimneys and areas 2000m away from layered and other occurrences are taken as the abnormal areas

↓

2.2: Delineating the ranges of the prospect areas: delineating the prospect areas based on the prospecting indicators and diffusion ranges in the previous step, and marking the overlap areas of multiple kinds of abnormalities

↓

3.1: Delineating the prospect areas with closed curves: a single prospecting indicator characteristic is delineated as the prospect area, and the prospect area should contain all s all prospecting indicator abnormalities; when various types of prospecting indicators are distributed in adjacent areas (the positions overlap but do not completely overlap), all kinds of abnormal scopes are delineated within the prospect area

↓

3.2 Determining the grades of the prospect areas according to the grades of the prospecting indicators and the types of the prospect in indicators in the prospect areas: high-grade prospect areas can be nested in low-grade prospect areas, and low-grade prospect areas cannot be nested in high-grade prospect areas

FIG. 2

METHOD FOR DELINEATING EXPLORATION RESERVED AREAS OF DEEP-SEA POLYMETALLIC SULFIDE RESOURCES

TECHNICAL FIELD

The present application belongs to the technical field of exploration and development of deep-sea resources, and particularly relates to a method for delineating exploration reserved areas of deep-sea polymetallic sulfide resources.

BACKGROUND

A variety of hydrothermal products can be formed in the process of deep-sea hydrothermal activity, including hydrothermal fluid, hydrothermal plume, hydrothermal sulfide, hydrothermal altered rocks, metal-bearing sediments and living organisms at vents, etc. Hydrothermal sulfide is usually rich in Cu, Zn, Au, Ag and other metal elements, and is also called polymetallic sulfide. Polymetallic sulfide is a kind of polymetallic mineral resources that can be developed and utilized, and its reasonable development provides the possibility to meet the demand of human beings for polymetallic mineral resources. As an important potential resource, the exploration of deep-sea polymetallic sulfide resources has attracted much attention. Many international research projects have also carried out a large number of investigations and studies on the distribution, scale and metallogenic control factors of this kind of resources on the seabed. Generally formed in the open environment of the seabed, polymetallic sulfides are not only closely related to magmatism, fault structure and the like, but also influenced by the characteristics of seawater dynamics and hydrochemistry, resulting in complex formation conditions and various forms of deposits. At present, there is no systematic method for delineating exploration reserved areas of deep-sea polymetallic sulfide resources, which restricts the progress of exploration. It is urgent to formulate an appropriate exploration delineation strategy to guide further resource evaluation and prediction.

SUMMARY

The purpose of the present application is to provide a method for delineating exploration reserved areas of deep-sea polymetallic sulfides. Through the analysis of prospecting indicators, the grades of the prospect areas are determined and the exploration reserved areas are delineated through the grades of the prospect areas.

The technical solution of the present application is as follows: a method for delineating exploration reserved areas of deep-sea polymetallic sulfide resources, including the following steps:

Step 1, a stage of extracting and grading prospecting indicators, including extracting prospecting indicators of deep-sea sulfide resources, specifying the characteristics of the indicators and determining the grades of the indicators; wherein the specific steps are as follows:

Step 1.1: extracting the prospecting information of deep-sea polymetallic sulfide resources, mainly including (1) plume information, (2) geophysical information, (3) geochemical information, (4) biological information, (5) wall rock alteration information and (6) mineralized outcrop information; wherein the specific process is as follows: specifying the characteristics of the prospecting indicators; (1) the characteristics of plume information: high temperature-salinity, high turbidity, low redox potential, high methane, high dissolved $Mn^{2+}$ and $Fe^{2+}$, high He isotope and $^3He/^4He$ ratio, with the seawater elements within 100 m around as background values; (2) the characteristics of the geophysical information: weak magnetism, high polarization, low resistance and high density relative to the background values within 200 m from the seabed; (3) the characteristics of the geochemical information: Cu—Zn—Fe—Mn combination element anomaly, MSI(Al/(Al+Fe+Mn)) anomaly, Cu/Fe anomaly, and the like; (4) the characteristics of the biological information: typical hydrothermal organisms, including anemones, armored shrimp, mioga and mussels; (5) the characteristics of the wall rock alteration information: silicification, chloritization, epidotization, zeolitization, iddingsitization, serpentinization and carbonatization; (6) the characteristics of the mineralized outcrop information: polymetallic sulfide chimneys and polymetallic sediments;

Step 1.2: specifying the grades of the prospecting indicators according to the credibility of the prospecting information, wherein the grades of the prospecting indicators are from low to high as follows: (1) plume information, (2) geophysical information, (3) geochemical information, (4) biological information, (5) wall rock alteration information and (6) mineralized outcrop information;

Step 2: a stage of evaluating metallogenic prospect areas, including delineation of control ranges indicated by various prospecting indicators, and delineation of the prospect areas based on the prospecting indicators; wherein the specific steps are as follows:

Step 2.1: delineating the scopes of abnormal areas based on the prospecting indicators, which is specifically as follows: (1) plume information: firstly, excluding terrain areas higher than a water body anomaly near where the water body anomaly is discovered according to topographic data, and then tracing the plume information according to local flow field distribution characteristics so as to delineate the scopes of the water anomaly areas; (3) the geochemical information: delineating anomaly areas in different grades according to the number of sulfide particles found in sediments, the intensity of heavy mineral anomalies and the anomalies of Cu, Zn, Fe and Pb elements; (4) the biological information: areas that are 100 m away from the borders of the enrichment areas of anemones, armored shrimps, mioga and mussels or remains thereof are taken as the abnormal areas; (5) the wall rock alteration information: areas that are 2000 m away from rocks or sediments with grayish brown, brown, yellow and red color changes are taken as the abnormal areas; (6) the mineralized outcrop information: areas that are 800 m away from brown and reddish-brown sulfides with mound, chimney, layer and breccia shapes that are direct evidences of sulfide areas are taken as the abnormal areas; for distribution areas with hydrothermal opals, chimneys and the like, areas that are 500 m away from mounds and chimneys and areas 2000 m away from layered and other occurrences are taken as the abnormal areas;

Step 2.2: delineating the prospect areas with closed curves based on the prospecting information in the previous step and the delineation scopes of the abnormal areas, wherein a single prospecting indicator can be delineated as the prospect area; when the prospect area contains all prospecting indicators, and the positions of various types of prospecting indicators overlap, but the positions do not completely overlap, all kinds of abnormal scopes are delineated within the prospect area;

Step 3: a stage of delineation of the exploration reserved areas, including evaluation and classification of the prospecting information, delineating the grades of prospect areas, and taking prospect areas with higher grades as the exploration reserved areas in turn; wherein the specific steps are as follows:

Step 3.1: dividing the grades of the prospect areas into grade I, grade II and grade III sequentially in terms of resource potentials from high to low according to the types of the prospecting information and the grades of the prospecting information in the prospect areas, wherein low-grade prospect areas can contain high-grade prospect areas, and high-grade prospect areas cannot contain low-grade prospect areas;

Step 3.2: delineating the exploration reserved areas according to the grades of the prospect areas.

Further, in the Step 2.1, the method for determining the scopes of the prospect areas based on the plumes further includes:

a distance D between a geographical location of the plume information and a hydrothermal source satisfying D≤a bottom velocity of seawater×a dissipation time of abnormal signals in seawater; wherein the hydrothermal source is located in an area below the water depth where plume information is found.

Further, in Step 2.1, the step of delineating abnormal areas in different grades according to element anomalies and heavy mineral anomalies further includes:

circularly rejecting specific values by means of an average+2×a variance until a data set meets requirements, wherein when the number of sulfide particles found in the sediments is more than 25, or the intensity of Cu and Zn element anomalies is greater than the average+2×the variance of a survey area, an area with a radius of 500-1000 m is delineated as a grade-I anomaly area; when the number of sulfide particles found in the sediments is more than 10, or the intensity of Cu and Zn element anomalies is greater than the average+the variance of the survey area, an area with a radius of 1500-2000 m is delineated as a grade-II anomaly area; and when the number of sulfide particles found in the sediments is more than 1, or the intensity of Cu and Zn element anomalies is greater than the average+0.5×the variance of the survey area, an area with a radius of 5000 m is delineated as a grade-III anomaly area.

Further, in Step 3.1, the step of delineating the prospect areas according to the prospecting indicators further includes:

a distance between two prospect areas being not less than 2 km: if the distance between two or more prospect areas in a same grade is less than 2 km, the areas are delineated as a same prospect area; if the distance between two or more prospect areas in different grades is less than 2 km, the areas are classified as nested prospect areas.

Further, in Step 3.2, the step of determining the grades of the prospect areas according to the grades of the prospecting indicators further includes:

dividing ore-forming indicators into three categories, indirect information: (1) plume information; metallogenic factor information: (2) geophysical information, (3) geochemical information and (4) biological information; and direct information: (5) wall rock alteration information and (6) mineralized outcrop information;

delineating areas with the direct information in the prospect areas as the grade-I prospect areas; delineating areas with the indirect information in the prospect areas as grade-II prospect areas; if there is metallogenic factor information in the prospect areas, delineating the prospect areas as grade-III prospect areas.

The present application has the beneficial technical effects that the method for delineating exploration reserved areas of deep-sea polymetallic sulfides provided by the present application has carried out the delineation of the exploration reserved areas in the polymetallic sulfide mining area in the southwest Indian Ocean, and based on the prospecting information, it can effectively determine the grades of the prospect areas, provide a basis for delineating the reserved areas, and has strong applicability, and has guiding significance for the exploration of polymetallic sulfide resources in other deep-sea areas.

BRIEF DESCRIPTION OF DRAWINGS

FIG. 2 shows the specific steps of a method for delineating exploration reserved areas of deep-sea polymetallic sulfide resources provided by the present application.

DESCRIPTION OF EMBODIMENTS

Figure 1:
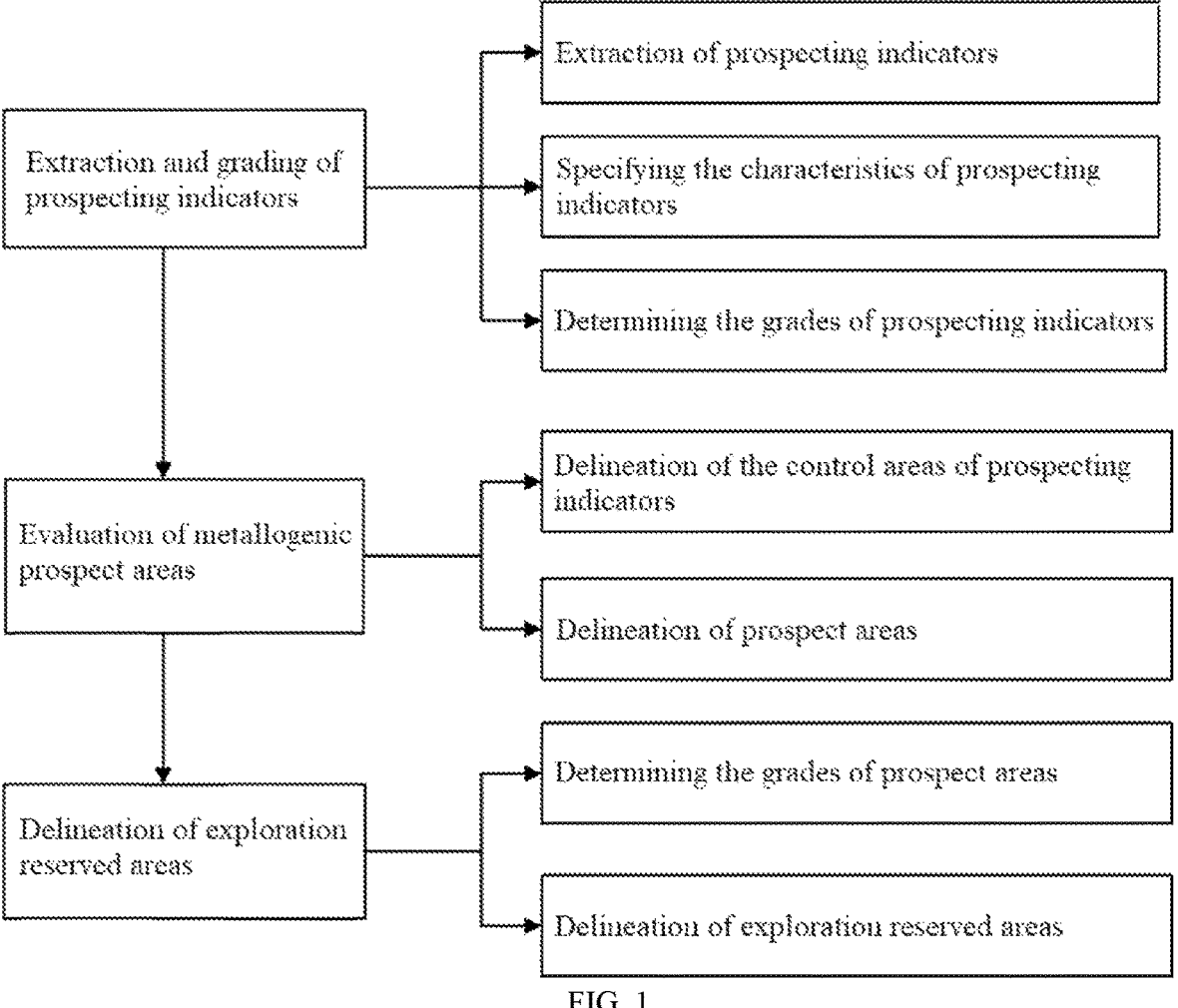
FIG. 1 is a flow chart of a method for delineating exploration reserved areas of deep-sea polymetallic sulfide resources provided by the present application.

The implementation of the method for delineating the exploration reserved areas of deep-sea polymetallic sulfide resources according to the present application will be described in detail with reference to the drawings and examples:

In the method for delineating the exploration reserved areas of deep-sea polymetallic sulfide resources, taking a certain prospect area A as an example, it can be divided into three sub-areas, A1, A2 and A3, with slightly different investigation degrees. The specific steps of delineating the exploration reserved area in this area include:

Step 1, a stage of extracting and grading prospecting indicators, including extracting prospecting indicators of deep-sea sulfide resources, specifying the characteristics of the indicators and determining the grades of the indicators;

Step 2: a stage of evaluating metallogenic prospect areas, including delineation of control ranges indicated by various prospecting indicators, and delineation of the prospect areas based on the prospecting indicators;

Step 3: a stage of delineation of the exploration reserved areas, including evaluation and classification of the prospecting information, delineating the grades of prospect areas, and taking prospect areas with higher grades as the exploration reserved areas in turn.

The specific steps of the Step 1 are as follows:

Step 1.1: extracting six kinds of prospecting indicators of deep-sea polymetallic sulfide resources, which are (1) plume information, (2) geophysical information, (3) geochemical information, (4) biological information, (5) wall rock alteration information and (6) mineralized outcrop information;

Step 1.2: specifying the characteristics of the prospecting indicators; (1) the characteristics of plume information: high temperature-salinity, high turbidity, low redox potential, high methane, high dissolved $Mn^{2+}$ and $Fe^{2+}$, high He isotope and $^3He/^4He$ ratio, with the seawater elements within 100 m around as background values;

(2) the characteristics of the geophysical information: weak magnetism, high polarization, low resistance and high density relative to the background values within 200 m from the seabed; (3) the characteristics of the geochemical information: Cu—Zn—Fe—Mn combination element anomaly, MSI(Al/(Al+Fe+Mn)) anomaly, Cu/Fe anomaly, and the like; (4) the characteristics of the biological information: typical hydrothermal organisms, including anemones, armored shrimp, mioga and mussels; (5) the characteristics of the wall rock alteration information: silicification, chloritization, epidotization, zeolitization, iddingsitization, serpentinization and carbonatization; (6) the characteristics of the mineralized outcrop information: polymetallic sulfide chimneys and polymetallic sediments;

Step 1.3: specifying the grades of the prospecting indicators according to the credibility of the prospecting information, wherein the grades of the prospecting indicators are from low to high as follows: (1) plume information, (2) geophysical information, (3) geochemical information, (4) biological information, (5) wall rock alteration information and (6) mineralized outcrop information.

The specific steps of the Step 2 are as follows:

Step 2.1: extrapolating the distribution ranges of the prospect areas based on the prospecting indicators, which is specifically as follows:

(1) plume information: both turbidity anomalies and dissolved methane gas anomalies are found in the area A1;

(2) geophysical information: magnetic detection results show that there is low magnetic anomaly in the area A2, and demagnetization is caused by the alteration of the heated liquid;

(3) geochemical information: the sulfide samples collected in the area A2 have low Cu and Zn contents, with the Cu content ranging from 0.02 wt. % to 2.88 wt. % and the Zn content generally lower than 0.01 wt. %; according to the contents of Cu, Fe and Si, they can be classified into a Si—Fe type;

(4) biological information: the remains of suspected hydrothermal organisms, such as mussels, snails, mioga, etc. are found in the area A2, and they are mainly distributed in the highland of seabed topography and its edge or mountainous areas, and their formation may be affected by the hydrothermal fluid;

(5) wall rock alteration information: the rocks are mainly basalt and peridotite in the area A3; basalt is gray-black, pillow-shaped and breccia-shaped, and altered in different degrees; the surface of the altered basalt is light green and yellow-green, while peridotite is light green, mostly with a breccia distribution; the alteration area is distributed around the mineralized area, and its strike is also northeast, showing an oval shape; the whole alteration area is about 500 m long and 250 m wide along the strike;

(6) mineralized outcrop information: in A3 area, massive sulfide and reddish-brown hydrothermal deposits are exposed, with a length of 200 m and a width of 100 m along the strike.

The method for determining the range of the prospect area based on plume further includes:

the distance D between a geographical location of the plume information and a hydrothermal source satisfying D≤a bottom velocity of seawater×a dissipation time of abnormal signals in seawater; wherein the hydrothermal source must be located in an area lower than the water depth where the abnormal signal of water body is found, that is, in the area where a hydrothermal anomaly signal is located, all the areas higher than the water depth where the hydrothermal anomaly signal is located can be basically excluded for the possibility of hydrothermal fluid sources.

The step of delineating abnormal areas in different grades according to element anomalies and heavy mineral anomalies further includes:

circularly rejecting specific values by means of an average+2×a variance until a data set meets requirements, wherein when the number of sulfide particles found in the sediments is more than 25, or the intensity of Cu and Zn element anomalies is greater than the average+2×the variance of a survey area, an area with a radius of 500-1000 m is delineated as a grade-I anomaly area; when the number of sulfide particles found in the sediments is more than 10, or the intensity of Cu and Zn element anomalies is greater than the average+the variance of the survey area, an area with a radius of 1500-2000 m is delineated as a grade-II anomaly area; and when the number of sulfide particles found in the sediments is more than 1, or the intensity of Cu and Zn element anomalies is greater than the average+0.5×the variance of the survey area, an area with a radius of 5000 m is delineated as a grade-III anomaly area.

Step 2.2: delineating the prospect areas with closed curves based on the prospecting information in the previous step and the delineation scopes of the abnormal areas, wherein a single prospecting indicator can be delineated as the prospect area; when the prospect area contains all prospecting indicators, and various types of prospecting indicators are distributed in adjacent areas (the positions overlap but do not completely overlap), all kinds of abnormal scopes are delineated within the prospect area.

The specific steps of the Step 3 are as follows:

Step 3.1: dividing the grades of the prospect areas into grade I, grade II and grade III sequentially in terms of resource potentials from high to low according to the types of the prospecting information and the grades of the prospecting information in the prospect areas, wherein high-grade prospect areas can be nested in low-grade prospect areas, and low-grade prospect areas cannot be nested in high-grade prospect areas.

The step of delineating the prospect areas according to the prospecting indicators further includes:

a distance between two prospect areas being not less than 2 km: if the distance between two or more prospect areas in a same grade is less than 2 km, the areas are delineated as a same prospect area; if the distance between two or more prospect areas in different grades is less than 2 km, the areas are classified as nested prospect areas.

Step 3.2: delineating the exploration reserved areas according to the grades of the prospect areas; the step of determining the grades of the prospect areas according to the grades of the prospecting indicators further includes:

dividing ore-forming indicators into three categories, indirect information: (1) plume information; metallogenic factor information: (2) geophysical information, (3) geochemical information and (4) biological information; and direct information: (5) wall rock alteration information and (6) mineralized outcrop information; delineating areas with the direct information in the prospect areas as the grade-I prospect areas; delineating areas with the indirect information in the prospect areas as grade-II prospect areas; if there is metallogenic factor information in the prospect areas, delineating the prospect areas as grade-III prospect areas; the area A1 is delineated as a grade-III prospect area; the area A2 is delineated as a grade-II prospect area; the area A3 is delineated as a grade-I prospect area.

The above examples are used to illustrate, rather than to limit, the present application. Any modifications and changes made to the present application within the scope of protection of the spirit and claims of the present application will fall within the scope of protection of the present application.

What is claimed is:

1. A method for delineating exploration reserved areas of deep-sea polymetallic sulfide resources, comprising the following steps:

Step 1, a stage of extracting and grading prospecting indicators, including extracting prospecting indicators of deep-sea sulfide resources, specifying the characteristics of the indicators and determining the grades of the indicators; wherein the specific steps are as follows:

Step 1.1: during carrying out exploration operations for the deep-sea polymetallic sulfide resources in a target sea area, through measured data obtained by geological investigation, sampling tests, and geophysical and geochemical measurements, extracting the prospecting indicators of deep-sea polymetallic sulfide resources, including (1) plume information, (2) geophysical information, (3) geochemical information, (4) biological information, (5) wall rock alteration information and (6) mineralized outcrop information;

Step 1.2: specifying the characteristics of the prospecting indicators; (1) characteristics of the plume information: high temperature-salinity, high turbidity, low redox potential, high methane, high dissolved $Mn^{2+}$ and $Fe^{2+}$, high He isotope and $^3He/^4He$ ratio, with the seawater elements within 100 m around as background values; (2) the characteristics of the geophysical information: weak magnetism, high polarization, low resistance and high density relative to the background values within 200 m from the seabed; (3) the characteristics of the geochemical information: Cu—Zn—Fe—Mn combination element anomaly, metalliferous sediment index (MSI, calculated as $Al/(Al+Fe+Mn)$) anomaly, Cu/Fe anomaly; (4) the characteristics of the biological information: typical hydrothermal organisms, including anemones, armored shrimp, mioga and mussels; (5) the characteristics of the wall rock alteration information: silicification, chloritization, epidotization, zeolitization, iddingsitization, serpentinization and carbonatization; (6) the characteristics of the mineralized outcrop information: polymetallic sulfide chimneys and polymetallic sediments;

Step 1.3: specifying the grades of the prospecting indicators according to the credibility of the prospecting indicators, wherein the grades of the prospecting indicators are from low to high as follows: (1) plume information, (2) geophysical information, (3) geochemical information, (4) biological information, (5) wall rock alteration information and (6) mineralized outcrop information;

Step 2: a stage of evaluating metallogenic prospect areas, including delineation of control ranges indicated by various prospecting indicators, and delineation of the prospect areas based on the prospecting indicators; wherein the specific steps are as follows:

Step 2.1: delineating the scopes of abnormal areas based on the prospecting indicators, which is specifically as follows: (1) the plume information: firstly, excluding terrain areas higher than a water body anomaly near where the water body anomaly is discovered according to topographic data, and then tracing the plume information according to local flow field distribution characteristics so as to delineate the scopes of water abnormal areas; (2) geophysical information: delineating magnetic abnormal areas according to magnetic detection result; (3) the geochemical information: delineating geochemical information abnormal areas in different grades according to the number of sulfide particles found in sediments, and the intensity of heavy mineral anomalies and the anomalies of Cu, Zn, Fe and Pb elements; (4) the biological information: areas that are 100 m away from the borders of enrichment areas of anemones, armored shrimps, mioga and mussels or remains thereof are taken as biological abnormal areas; (5) the wall rock alteration information: areas that are 2000 m away from rocks or sediments with grayish brown, brown, yellow and red color changes are taken as wall rock alteration abnormal areas; (6) the mineralized outcrop information: areas that are 800 m away from brown and reddish-brown sulfides with mound, chimney, layer and breccia shapes that are direct evidences of sulfide areas are taken as sulfide abnormal areas; for distribution areas with hydrothermal opals, chimneys, areas that are 500 m away from mounds and chimneys are taken as mounds and chimneys abnormal areas, and areas 2000 m away from layered and other occurrences are taken as layered occurrences abnormal areas;

Step 2.2: delineating the prospect areas with closed curves based on the prospecting indicators in the previous step and the delineation scopes of the abnormal areas, wherein a single prospecting indicator can be delineated as a prospect area; when the prospect area contains all prospecting indicators, and the positions of various types of prospecting indicators overlap, but the positions do not completely overlap, all kinds of abnormal scopes are delineated within the prospect area;

Step 3: a stage of delineation of the exploration reserved areas, including evaluation and classification of the prospecting indicators, delineating grades of the prospect areas, and taking prospect areas with higher grades as the exploration reserved areas in turn; wherein the specific steps are as follows:

Step 3.1: dividing the grades of the prospect areas into grade I, grade II and grade III sequentially in terms of resource potentials from high to low according to the types of the prospecting indicators and the grades of the prospecting indicators in the prospect areas, wherein low-grade prospect areas can contain high-grade prospect areas, and high-grade prospect areas cannot contain low-grade prospect areas;

Step 3.2: delineating the exploration reserved areas according to the grades of the prospect areas, and obtaining exploration reservation area delineation results for guiding subsequent exploration and resource evaluation of deep-sea polymetallic sulfide resources.

2. The method for delineating exploration reserved areas of deep-sea polymetallic sulfide resources according to claim 1, wherein in the Step 2.1, the method for determining the scopes of the prospect areas based on the plumes further comprises:

a distance D between a geographical location of the plume information and a hydrothermal source satisfies $D \le a$ bottom velocity of seawater×a dissipation time of abnormal signals in seawater; wherein the hydrothermal source is located in an area below the water depth where plume information is found.

3. The method for delineating exploration reserved areas of deep-sea polymetallic sulfide resources according to claim 1, wherein in the Step 2.1, the step of delineating abnormal areas in different grades according to element anomalies and heavy mineral anomalies further comprises:

circularly rejecting specific values by means of an average+2×a variance until a data set meets requirements, wherein when the number of sulfide particles found in the sediments is more than 25, or the intensity of Cu and Zn element anomalies is greater than the average+ 2× the variance of a survey area, an area with a radius of 500 m-1000 m is delineated as a grade-I abnormal area; when the number of sulfide particles found in the sediments is more than 10, or the intensity of Cu and Zn element anomalies is greater than the average+the variance of the survey area, an area with a radius of 1500 m-2000 m is delineated as a grade-II abnormal area; and when the number of sulfide particles found in the sediments is more than 1, or the intensity of Cu and Zn element anomalies is greater than the average+0.5×the variance of the survey area, an area with a radius of 5000 m is delineated as a grade-III abnormal area.

4. The method for delineating exploration reserved areas of deep-sea polymetallic sulfide resources according to claim 1, wherein in the Step 3.1, the step of delineating the prospect areas according to the prospecting indicators further comprises:

when a distance between two or more prospect areas is not less than 2 km; if the two or more prospect areas are in a same grade, delineating the two or more prospects areas as a same prospect area; and if the two or more prospect areas are in different grades, delineating the two or more prospects areas as nested prospect areas.

5. The method for delineating exploration reserved areas of deep-sea polymetallic sulfide resources according to claim 1, wherein in the Step 3.2, the step of determining the grades of the prospect areas according to the grades of the prospecting indicators further comprises:

dividing ore-forming indicators into three categories, indirect information: (1) plume information; metallogenic factor information: (2) geophysical information, (3) geochemical information and (4) biological information; and direct information: (5) wall rock alteration information and (6) mineralized outcrop information; delineating areas with the direct information in the prospect areas as the grade-I prospect areas; delineating areas with the indirect information in the prospect areas as grade-II prospect areas; if there is metallogenic factor information in the prospect areas, delineating the prospect areas as grade-III prospect areas.

* * * * *